United States Patent
Zhuge et al.

(10) Patent No.: US 10,386,339 B2
(45) Date of Patent: Aug. 20, 2019

(54) MODAL VIBRATION ANALYSIS SYSTEM

(71) Applicant: Crystal Instruments Corporation, Santa Clara, CA (US)

(72) Inventors: James Q Zhuge, Palo Ato, CA (US); Weijie Zhao, Los Gatos, CA (US)

(73) Assignee: Crystal Instruments Corporation, Santa Clara, CA (US)

( * ) Notice: Subject to any disclaimer, the term of this patent is extended or adjusted under 35 U.S.C. 154(b) by 126 days.

(21) Appl. No.: 15/668,995

(22) Filed: Aug. 4, 2017

(65) Prior Publication Data

US 2019/0041365 A1 Feb. 7, 2019

(51) Int. Cl.
*G01N 29/46* (2006.01)
*G01N 29/04* (2006.01)

(52) U.S. Cl.
CPC ........... *G01N 29/46* (2013.01); *G01N 29/045* (2013.01); *G01N 2291/014* (2013.01); *G01N 2291/0258* (2013.01); *G01N 2291/042* (2013.01)

(58) Field of Classification Search
CPC ............. G01N 29/46; G01N 2291/042; G01N 2291/04; G01N 2291/0258; G01N 2291/014
See application file for complete search history.

(56) References Cited

U.S. PATENT DOCUMENTS

| | | |
|---|---|---|
| RE34,663 E | 7/1994 | Seale |
| 5,533,399 A | 7/1996 | Gibson et al. |
| 5,614,720 A | 3/1997 | Morgan et al. |
| 5,841,030 A | 11/1998 | Honsberg et al. |
| 6,574,570 B1 | 6/2003 | Sato et al. |
| 6,684,168 B1 | 1/2004 | Kawamoto et al. |
| 6,779,404 B1 | 8/2004 | Brincker et al. |
| 6,810,741 B1 | 11/2004 | Lafleur et al. |
| 7,725,274 B2 | 5/2010 | Slemp et al. |
| 8,494,790 B2 | 7/2013 | Zhu et al. |
| 2002/0186895 A1 | 12/2002 | Gloersen |

(Continued)

OTHER PUBLICATIONS

Li et al., Precise Measurement of Natural Frequencies and Mode Shapes of Cantilever Thin Cylindrical Shell, Aug. 2015, Journal of Vibration Engineering & Technologies, vol. 3, No. 4, pp. 513-537 (Year: 2015).*

*Primary Examiner* — Toan M Le
(74) *Attorney, Agent, or Firm* — Thomas Schneck

(57) ABSTRACT

A modal vibration analysis system and corresponding method is provided. Exciters are coupled to a structure under test for generating vibrations in the structure. Sensors are coupled to the structure at multiple locations for sensing vibrations generated in response to the excitations. A controller provides drive signals to the exciters such that the sensor signals have a target output spectrum with specified characteristics in multiple designated frequency domains of the spectrum, characterized by a random phase for each frequency. Modal analysis processes digitized sensor signals with a Fast Fourier Transform conducted at two or more specified data sampling rates to synthesize a spectrum containing data points with finer frequency resolution for lower frequency range, and regular frequency resolution for higher frequency range. From the multi-resolution spectra, natural frequencies and damping coefficients are determined at each mode, and a mode shape at each natural frequency is computed.

17 Claims, 3 Drawing Sheets

(56) References Cited

U.S. PATENT DOCUMENTS

2009/0326419 A1 12/2009 Gonzalez Rojas et al.
2014/0100798 A1 4/2014 Guan et al.
2016/0355278 A1 12/2016 Goodman
2017/0122835 A1 5/2017 Bakker et al.

* cited by examiner

MODAL VIBRATION ANALYSIS SYSTEM

TECHNICAL FIELD

The present invention relates to systems and methods for modal analysis of sensed vibration data obtained from vibration testing of structures, and in particular to modal analysis of spectra data obtained from multiple input channels and with multiple frequency resolutions to extract natural frequencies, damping values, modal shapes, and other information from the measured data.

BACKGROUND ART

In a typical structure, there are many vibration modes over a wide range of frequencies. One important goal of modal analysis is to identify and properly characterize each of these modes. The bandwidths of the various modes are governed by two parameters, one being the natural frequency itself and the other being the quality factor Q. If the Q value is fixed, then bandwidth is only proportional to the natural frequency. For example, with a similar Q value, the bandwidth of a resonance at 1000 Hz frequency can be as wide as a few dozen up to a hundred Hertz, while for a resonance in the 1.0 to 10 Hz frequency range, the bandwidth can be as narrow as less than one Hertz. Because of this, most characteristics of a dynamic mechanical system are better described using different resolutions in the frequency axis, needing higher analysis frequency resolution for lower natural frequency modes.

In a multi-input multi-output (MIMO) test, multiple exciters and multiple measurement sensors are configured. Excitation signals will have a broadband excitation energy and usually have a random nature, e.g. random, pseudo-random, burst random, chirp, periodic random, white noise, pink noise etc. A first requirement for modal analysis of MIMO test results is to measure the frequency response functions of the structure under test. When a traditional Fast Fourier Transform (FFT) method is used, the frequency resolution is always uniform across the whole frequency range covered by the transformation. Assuming, for a typical setup, that the test goes up to 2000 Hz vibration frequency, 2048 points of time block, and 800 frequency lines of FFT spectrum are sampled at a rate of 5120 Hz, the FFT method will provide a resolution for the frequency response function of (2000/800) Hz=2.5 Hz. Due to the nature of structural vibrations, such resolution, while sufficient for higher frequency modes, is not suitable for any modes of less than about 100 Hz.

If, instead, we increase the resolution tenfold to 0.25 Hz to be able to properly characterize low frequency modes, then the data capture size to perform the FFT must also increase tenfold. Considering that in a typical modal analysis project that hundreds or thousands of sensor signals are acquired, increasing the already large size of the data array to be stored by an order of magnitude is not at all desirable, particularly since much of that data is simply wasted at the higher frequency modes. Not only does the increase of FFT size create a storage issue for the data, but since time for data capture is proportional to its size, the testing duration will also need to increase tenfold. The time needed for FFT processing of the extra data will likewise increase. Still further, unless we adopt some different excitation technology, there may not be enough excitation energy in the low frequency band to generate a usable response, and the strategy of increasing FFT size will still produce unsatisfactory results.

Several different methods have been chosen to deal with these problems. One common approach is to conduct the modal tests multiple times at different frequency ranges. For example, in one round of testing, the excitation frequency range could be set to 2000 Hz and all resonance modes at or above 100 Hz identified, and in another round of testing, the excitation frequency range could then be set to 100 Hz to identify the low frequency resonance modes. When the frequency range is set differently, the energy of the excitation signals will adjust accordingly, so the same FFT resolution can be used while still obtaining good accuracy for the frequency response function at all tested frequencies. However, each modal test is already a very time-consuming process. Due to the limited number of sensors and input channels usually available, a typical test needing 200 measurement points (i.e. sensor locations with directions) but using only eight sensors will conduct 25 measurements, moving the sensor locations 25 times, and take a few days to finish. Having to redo the test twice (or multiple times) for different frequency ranges will multiply the testing time. Additionally, testing data management becomes more complex, because test results for different frequency ranges are not stored and presented with integration.

Another common approach is to use either a swept or step sine excitation in place of random excitation. A sine test allows the excitation of a structure to sequentially concentrate upon one frequency at a time. Swept sine uses a continuously changing frequency, while in a stepped sine test the excitation dwells for a time at each frequency then steps or increments to the next frequency. The main disadvantage with either of these sine methods is that it takes even longer time, each sweep or stepping through of a test frequency range taking hours to finish, especially at low frequency where the sweeping is slower or the step increments are smaller. Another disadvantage is that structures often exhibit complex nonlinear behaviors (mode coupling) when many modes of vibration occurring at the same time interfere with each other. Because the sine test sequentially excites only one frequency at a time, it cannot adequately reproduce the actual environment where structures are simultaneously excited across a wide band of frequencies.

The discussion above describes the need to have different analysis frequency resolution to analyze the spectral data over the frequency range of interest. In fact, there is also a need to have more than one exciter to generate the vibration with different energy distribution at different frequency range. For example, for a large aircraft structure testing, it may be desired to use a hydraulic shaker to generate very large displacement in the frequency range of less than 10 Hz, while an electro-dynamic exciter is used to generate the vibration above 10 Hz. When multiple shakers are used, the shape of output force spectra, or summation of them, should be controlled. The previous techniques using multi-exciters did not address the demand of using different frequency resolution to analyze the data.

SUMMARY DISCLOSURE

A modal vibration analysis system is provided that allows one to extract and visualize all vibration modes with only a single test run. The system includes a set of exciters coupled to a unit under test for generating vibrations in such a structure, and a set of sensors coupled to the unit or structure under test at multiple locations for sensing the vibrations and excitation reference(s) generated in response to the excitations. A controller receives sensor signals corresponding to the sensed vibrations from the set of sensors and provides drive signals to the set of exciters, such that the sensor signals have a target output spectrum with specified characteristics in multiple designated frequency domains of the spectrum, wherein the set of exciters simultaneously generate broadband vibration in the structure. A modal analysis processor receives the excitation reference and sensor signals and then, from these signals, computes a set of frequency response functions for the structure covering the whole frequency range for all sensor locations, determines natural frequencies as well as damping coefficients, and computes a mode shape at each natural frequency using all measured data from all sensor locations. This modal analysis is a multi-resolution analysis carried out at higher resolution for lower frequency range, and regular resolution for higher frequency range.

DETAILED DESCRIPTION

Figure 1:
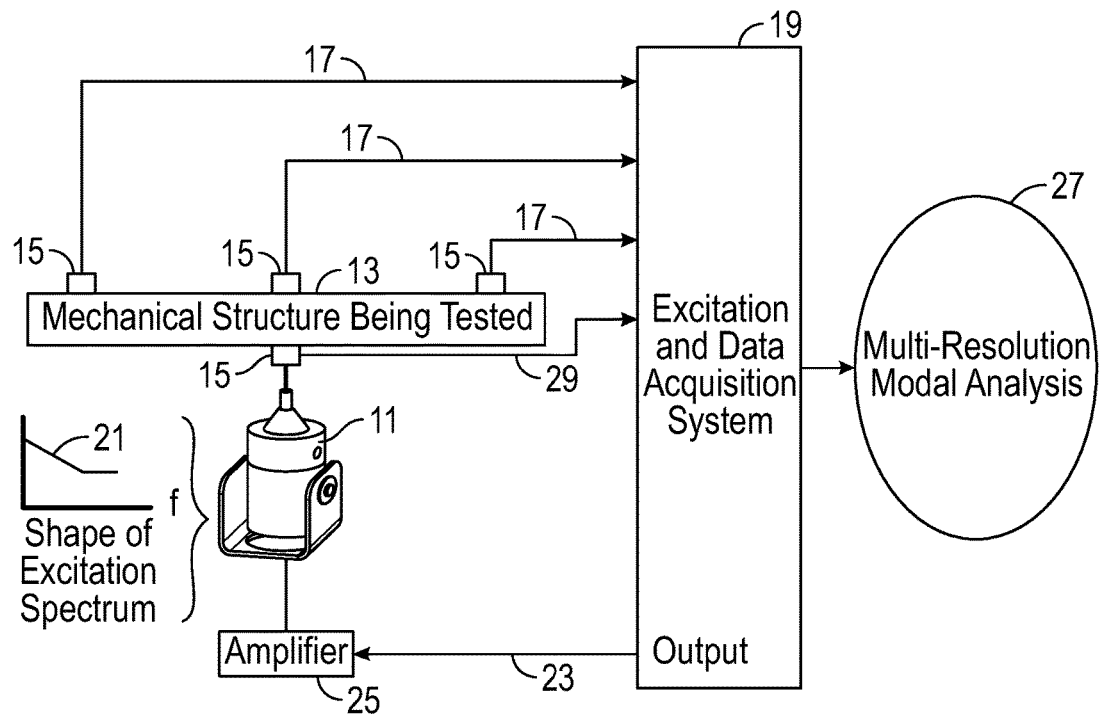
FIG. 1 is a schematic plan view of a first testing system in accord with the present invention which employs a single exciter, wherein its driving spectrum (the shape of the excitation energy versus frequency) is controlled. Multiple sensors provide measurement input for modal analysis.

With reference to FIG. 1, in one embodiment of a testing system according to the present invention, a single exciter 11 provides the vibrational excitation energy to a mechanical structure 13 being tested. Multiple sensors 15 on the structure measure the vibration at various positions and excitation reference, providing measurement inputs 17 and 29 to an excitation and data acquisition system 19. The system 19 processes the measurement data 17, using it as feedback for comparison with a targeted excitation spectrum 21, to provide an excitation output 23 to an amplifier 25 driving the exciter 11. In this way, the excitation energy of a random signal can be controlled over the frequency range. The measurement inputs 17 and excitation reference 29 are also provided to an analysis system 27 for obtaining multi-resolution spectra and performing modal analysis on the basis of such spectra.

Figure 2:
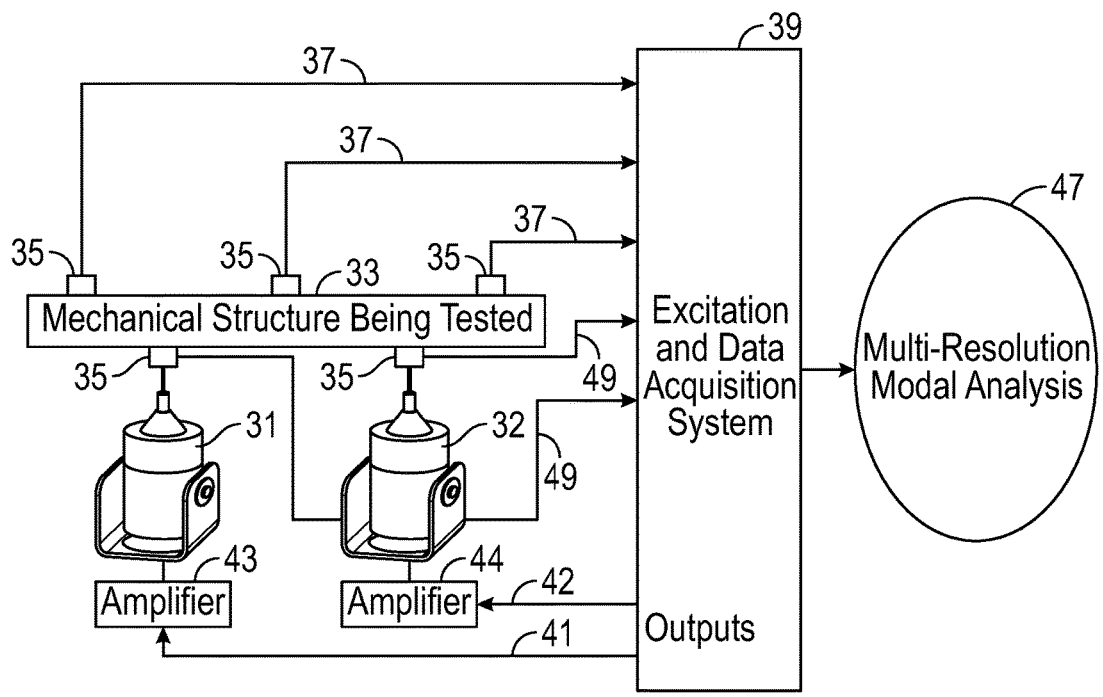
FIG. 2 is a schematic plan view of a second testing system in accord with the present invention which employs two (or more) exciters that each excite over a particular frequency range. Again, multiple sensors provide measurement input for modal analysis.

With reference to FIG. 2, in another embodiment of a testing system according to the present invention, multiple (two or more) exciters 31 and 32 can be used to provide the vibrational excitation energy to a mechanical structure 33 being tested, wherein each exciter 31 and 32 excites a different range of frequencies. Multiple sensors 35 on the structure 33 measure the vibration at various positions and the excitation references, providing measurement inputs 37 and excitation references 49 to an excitation and data acquisition system 39. The system 39 processes the measurement data 37, using it as feedback for comparison with a targeted excitation spectrum, to provide an excitation outputs 41 and 42 to amplifiers 43 and 44 that drive the respective exciters 31 and 32. In this way, the excitation energy of a random signal can be controlled over the frequency range. The summation of the spectra for the exciters 31 and 32 create an overall composite spectrum whose shape (energy versus frequency) is controllable over the entire frequency range of all exciters. The measurement inputs 37 and excitation references 49 are also provided to an analysis system 47 for obtaining multi-resolution spectra and performing modal analysis on the basis of such spectra.

In the embodiments of FIGS. 1 and 2, one or more modal exciters 11, 31, 32 are used in the modal testing to apply force to the mechanical structure 13, 33 being tested. Each exciter 11, 31, 32 is connected to a power amplifier 25, 43, 44, which in turn is connected to the output terminal of the dynamic measurement system 19, 39. Multiple sensors 15, 35 are attached to the structure being tested. Typically, the sensors are of the accelerometer type, but other types, such as displacement sensors or velocity sensors, could also be used. The excitation references are measured using force sensors.

The dynamic measurement system 19, 39 will send out the excitation signals 23, 41, 42 to each exciter and drive the vibration of the structure. Sensors will then measure the vibration and send the analog signals 17, 29, 37, 49 back to the dynamic measurement system. Inside of dynamic measurement system 19, 39, multiple A/D converters will convert the analog signals into digital form, and a digital signal processor or CPU processor will process the sensor data and compute the multiple FRF signals simultaneously.

In this invention, all excitation signals will have random nature. Random signals will excite the structure under test over a broadband frequency range. When one single exciter 11 is used, the spectrum shape of excitation signal will be controllable, meaning the user can define the shape (energy versus frequency) of such a random signal. When two or more exciters 31, 32 are used, the summation of the spectra of each excitation signals will be controllable. Each channel 41, 42 of excitation will have energy in a different frequency band. For example, one of the exciters 41 will output vibrations that have energy in a range above 100 Hz, while the other exciter 42 will create the vibration energy at less than 100 Hz. In fact, the mechanism of exciter can be different because the frequency range requirement is different. Hydraulic shakers are better at generating vibration at very low frequency, while electrical dynamic shakers are good at generating higher frequency. The excitation energy of these exciters can overlap because the multiple resolution analysis algorithm developed for this invention does not require that they have to be cleanly separated.

After the data of multiple sensor channels 17, 29, 37 and 49 are acquired, they will be fed into a data analysis system 27, 47 executing a new algorithm called multi-resolution modal analysis. Multi-resolution modal analysis consists of two parts: 1) multi-resolution spectrum analysis, i.e., estimate, store and present the frequency response function (FRF) in multi-resolution fashion, and 2) modal analysis that can be applied to the FRFs stored in multi-resolution format. The multi-resolution modal analysis provides accurate modal estimation over a wide range of frequencies, without the problems of prior approaches. For example, test time is the same as that of conventional MIMO test, and far less than either running the test multiple times at different frequency ranges or employing swept or stepped sine testing. The management of testing results are fully integrated. The presentation of graphic display for both high and low frequency is as easy as that of a conventional uniform resolution method, but with greater accuracy at low frequencies.

Figure 3:
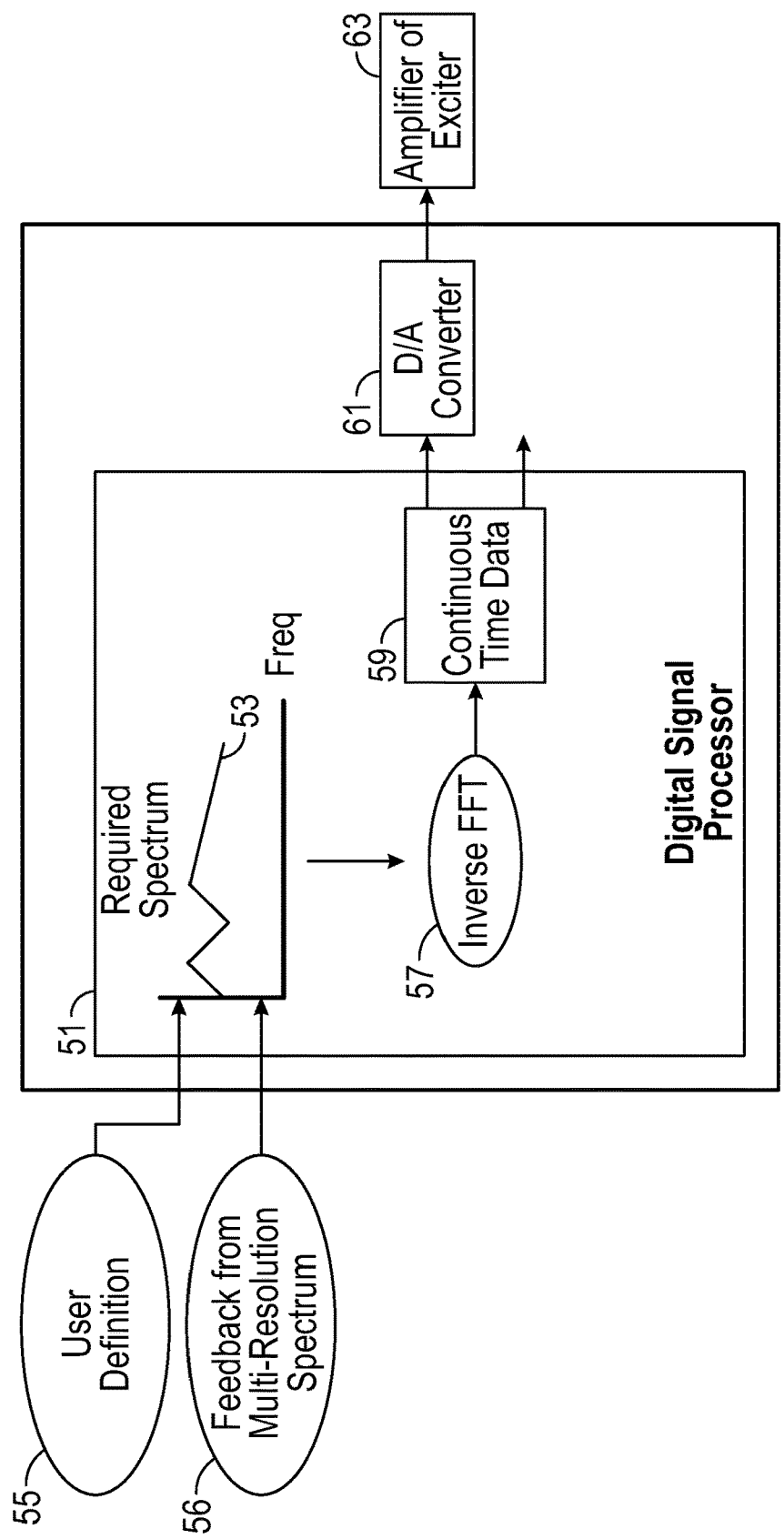
FIG. 3 is a schematic plan view of driver processing hardware for providing control of excitation with defined spectrum characteristics.

With reference to FIG. 3, the hardware aspect of the output path for generating a random excitation output in which the spectrum shape can be controlled (a key part of the dynamic measurement system 19, 39 of FIGS. 1 and 2) is schematically shown. A random signal, which has frequency content over a wide frequency range, can have different spectrum shapes. White noise is a random signal that have "flat" spectrum shape, i.e. essentially the same energy applied across the entire spectrum. Pink noise is a random signal that has "−3 dB" slope of spectrum shape. The hardware executes an algorithm that creates a random signal that meets any desired spectrum shape definition. First, the user defines the frequency spectrum shape using a breakpoint table. This is user definition 55 input to a digital signal processor 51 as a required spectrum 53. For example, a user may decide to excite the structure between 1 Hz to 10 Hz with 10 lbs (rms) of force, but between 10 Hz to 100 Hz with 20 lbs (rms) of force. This can also be decided by other targets, such as displacement of the exciter, provided the sensors measure in the target units. The required spectrum 53 is used to generate continuous time data 59 that has such defined spectrum characteristics. A random phase is assigned to each frequency point, and then inverse Fast Fourier Transform (inverse-FFT) 57 and overlapping processes are applied to the spectrum to generate a continuous random signal 59 that meets the spectrum shape requirement. Overlapping portions of the spectrum can be apportioned between the relevant exciters in any way desired, provided the sum of the applied energy at each frequency achieves the desired total for that frequency. Continuous time data 59 will be sent to one or multiple D/A converters 61. After D/A conversion of the signals into analog form, they can be sent to the input end of the exciter amplifier(s) 63.

The required spectrum comes from two sources: one is from the intervention of the user (the spectrum shape definition 55), while the other is feedback from the sensors' measurement data 56. A coherence function estimated from the multi-spectra will indicate the confidence level of the accuracy of spectrum. Based on the coherence function that is described in multi-resolution format, the required spectrum can be automatically tuned.

Figure 4:
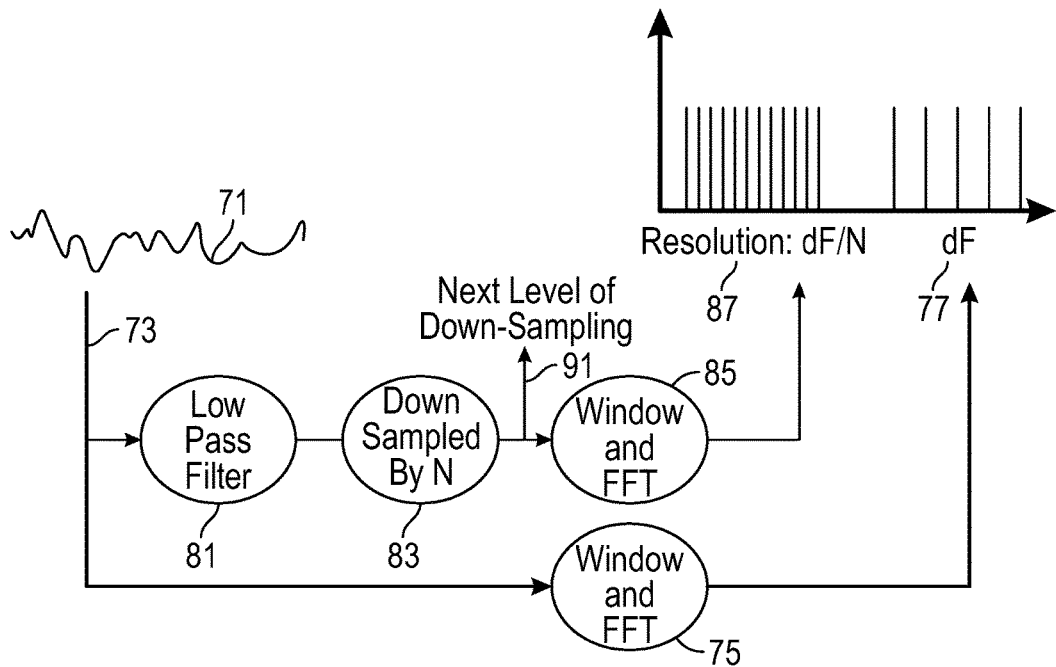
FIG. 4 is a schematic plan view illustrating multi-resolution spectrum analysis of sensor data.

With reference to FIG. 4, the multi-resolution spectrum analysis system (27 in the embodiment of FIG. 1, 47 in the embodiment of FIG. 2) is based on Fast Fourier Transform (FFT) spectrum analysis, but instead generates the frequency spectrum as a composite that merges several spectra with different resolutions for different frequency bands. The FFT spectrum within any given frequency band has a uniform frequency resolution. But, different frequency bands have different frequency resolutions, wherein a higher resolution is calculated for lower frequencies and lower resolutions are used at the higher frequencies.

FIG. 4 shows the signal 71 coming from one measurement channel. In practice, multiple channels of signals will be processed together. The digital data 73 coming from an A/D converter (not shown) shall go through certain signal conditioning, such as low pass or high pass filtering, to remove unwanted noise. Then it will be split into two paths. One path will go through conventional spectrum analysis algorithm 75, i.e., data windowing and FFT and averaging. The FFT spectrum 77 will be calculated. A second path, which is called down-sampling path, will first low filter 81 the signal. The cutoff frequency of low pass filter will be set so that the interested frequency range is within the cutoff frequency. Then the data will be down-sampled 83. Down-sampling by N means that for every N points one point will be used while N−1 points will be discarded. After the down-sampling, the data will go through spectrum analysis 85, i.e., windowing, FFT and averaging. Now the spectrum 87 from the second path will have a resolution that is N times finer. The algorithm will then synthesize two spectra together into a composite spectrum. The low frequency range of the first spectrum will be discarded and replaced with the content coming from the second spectrum, which has higher resolution.

The down-sampling process can be cascaded. The output of second path after the down-sampling 83 can be used as the input of another path 91. This means that, if desired, more than two spectra with different resolutions can be synthesized together.

The process above describes the basics of multi-resolution FFT spectrum analysis. Other spectral types, such as power spectrum, coherence spectrum, power spectral density, phase spectrum or frequency response function (FRF), can all be derived from the FFT spectrum with multi-resolution.

Figure 5:
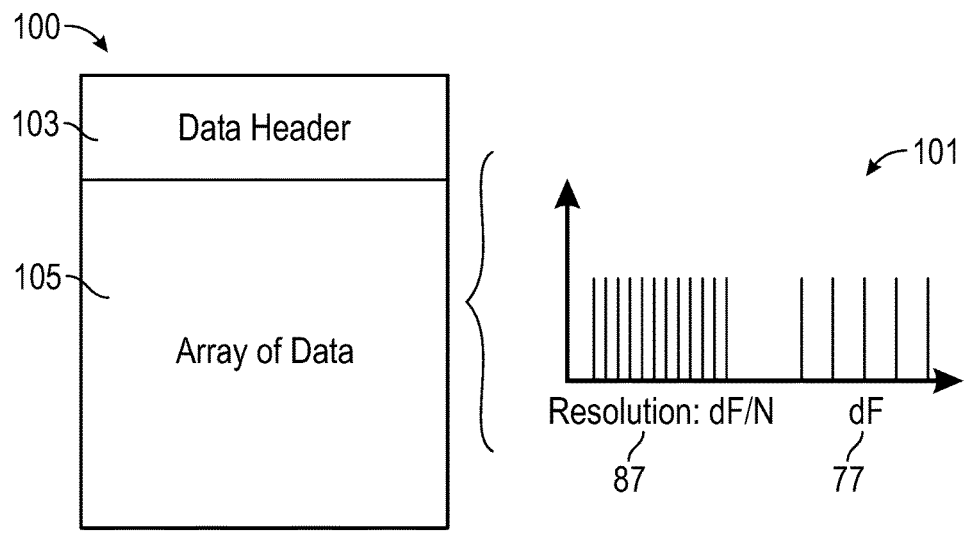
FIG. 5 is a schematic plan view illustrating a scheme to store and present multi-resolution measurements and modal analysis spectra in an integrated manner.

With reference to FIG. 5, it is very important to store and present the spectrum 101 with multiple resolutions 77 and 87 in a convenient way, so the display and modal analysis can be applied easily. Usually, the signal data 100 is described by a header 103 that stores the attributes of the data. Then the large contiguous data array 105 follows the data header 103. Another way to store multi-resolution data is to first convert the signal into a data set that is logarithmic scaled on the frequency axis. Regardless, the data storage and presentation must accommodate the nature of non-uniform frequency resolution.

What is claimed is:

1. A modal vibration analysis system, comprising:
a set of one or more exciters coupled to a structure under test for generating vibrations in the structure;
a set of sensors coupled to the structure at multiple locations for sensing vibrations generated in the structure in response to excitation;
a controller receiving sensor signals corresponding to the sensed vibrations from the set of sensors and providing drive signals to the set of exciters such that the sensor signals have a target output spectrum with specified characteristics in multiple designated frequency domains of the spectrum, wherein the set of exciters simultaneously excite multiple coupled modes of vibration in the structure; and
a modal analysis system receiving the excitation reference signal and sensor signals to compute a set of frequency response functions for the structure at multiple frequencies and sensor locations, determine natural frequencies and damping coefficients at each mode, and compute a mode shape at each natural frequency, wherein the computation of frequency response functions is carried out in parallel paths at finer frequency resolution for lower frequency range.

2. The system as in claim 1, wherein each exciter is connected to an amplifier and the drive signals are provided to the set of one or more exciters via their corresponding amplifiers.

3. The system as in claim 1, wherein the drive signal provided to the set of exciters by the controller is characterized by a random phase for each frequency.

4. The system as in claim 1, wherein the set of exciters consists of a single exciter having a controlled spectrum shape of applied vibrational energy versus frequency.

5. The system as in claim 1, wherein the set of exciters comprises two or more exciters with vibrational outputs having a controlled summation of spectrum shapes of applied vibrational energy versus frequency.

6. The system as in claim 1, wherein sensor signals from the set of sensors are analog signals converted into digital form by a corresponding set of A/D converters in the controller, all A/D converters being synchronized by a common sampling clock.

7. The system as in claim 1, wherein the modal analysis system processes digitized sensor signals with data windowing and a Fast Fourier Transform (FFT) process conducted at two or more specified data sample rates to synthesize a spectrum containing data points at two or more frequency resolutions, the data points of the synthesized spectrum being stored in a contiguous array.

8. The system as in claim 1, wherein the modal analysis system is carried out at finer frequency resolution for lower frequency range by splitting digitized sensor signals into two or more data paths, all but one data path going through a low pass filter and down-sample process, digitized sensor signals in each data path, after any down-sampling, then undergoing data windowing and a Fast Fourier Transform (FFT) process to synthesis a spectrum for each data path, the spectra from each data path being merged into a composite spectrum containing data points at two or more frequency resolutions, the data points of the synthesized spectrum being stored in a contiguous array.

9. The system as in claim 1, wherein the modal analysis system determines natural frequencies and damping coefficients at each mode, and computes a mode shape of each mode, from a multi-resolution spectrum first synthesized from the sensor signals and excitation reference signals.

10. A method of preforming modal vibration analysis, comprising:

generating vibrations in a structure under test using a set of one or more exciters coupled to the structure;

sensing the generated vibrations by a set of sensors coupled to the structure at multiple locations and producing corresponding sensor signals, a controller responsive to the sensor signals providing drive signals to the set of exciters such that the sensor signals have a target output spectrum with specified characteristics in multiple designated frequency domains of the spectrum, wherein the set of exciters simultaneously generate all modes of vibration within the testing frequency range in the structure; and conducting modal analysis upon the sensor signals and excitation reference signal(s) to compute a set of frequency response functions for the structure at multiple frequencies and sensor locations, determine natural frequencies and damping coefficients at each mode, and compute a mode shape at each natural frequency, wherein the computation of frequency response functions is carried out in parallel paths at finer frequency resolution for lower frequency range.

11. The method as in claim 10, wherein the generated vibrations are characterized by a random phase for each frequency.

12. The method as in claim 10, wherein the vibrations are generated by a single exciter, the vibrations having a controlled spectrum shape of applied vibrational energy versus frequency.

13. The method as in claim 10, wherein the vibrations are generated by multiple exciters with vibrational outputs having a controlled summation of spectrum shapes of applied vibrational energy versus frequency.

14. The method as in claim 10, wherein sensor signals are converted into digital form synchronized by a common sampling clock.

15. The method as in claim 10, wherein the modal analysis comprises data windowing and a Fast Fourier Transform (FFT) process conducted at two or more specified data sample rates to synthesize a spectrum containing data points at two or more frequency resolutions, the data points of the synthesized spectrum being stored in a contiguous array.

16. The method as in claim 10, wherein the modal analysis is carried out at finer frequency resolution for lower frequency range by splitting digitized sensor signals into two or more data paths, all but one data path going through a low pass filter and down-sample process, digitized sensor signals in each data path, after any down-sampling, then undergoing data windowing and a Fast Fourier Transform (FFT) process to synthesis a spectrum for each data path, the spectra from each data path being merged into a composite spectrum containing data points at two or more frequency resolutions, the data points of the synthesized spectrum being stored in a contiguous array.

17. The method as in claim 10, wherein the modal analysis further determines the natural frequencies and damping coefficients at each mode, and computes the mode shape at each mode, from a multi-resolution spectrum first synthesized from the sensor signals and excitation references.

\* \* \* \* \*